United States Patent [19]
Mizutare et al.

[11] Patent Number: 5,679,830
[45] Date of Patent: Oct. 21, 1997

[54] METHOD OF PRODUCING PIVALOYLACETIC ACID ESTER

[75] Inventors: Katsuhiko Mizutare; Masayoshi Oku; Tsuyoshi Ueyama, all of Ube, Japan

[73] Assignee: Ube Industries, Ltd., Ube, Japan

[21] Appl. No.: 501,439

[22] Filed: Jul. 12, 1995

[30] Foreign Application Priority Data

Jul. 19, 1994 [JP] Japan ................................. 6-166910

[51] Int. Cl.$^6$ ........................ C07C 67/333; C07C 69/716
[52] U.S. Cl. ........................ 560/174; 560/176; 560/178
[58] Field of Search ........................ 560/176, 178, 560/174; 502/33

[56] References Cited

U.S. PATENT DOCUMENTS 2,527,306  10/1950  Halverstadt .
4,661,621   4/1987  Werner et al. .

FOREIGN PATENT DOCUMENTS 00288759  5/1981  European Pat. Off. .
56-83446   of 1981  Japan .

OTHER PUBLICATIONS

J. Org. Chem, 1991, vol. 56, No. 18, Emerson et al., Evidence for Ketene Intermediates in the Decarbonylation of 2,4-Dioxo Acids and Esters and 2-Oxobutanedioic Acid Esters.

David R. Lide, CRC Handbook of Chemistry and Physics, 71st edition, PP. 15–38 1990–91.

Primary Examiner—José G. Dees
Assistant Examiner—Rosalynd A. Williams
Attorney, Agent, or Firm—Burgess, Ryan & Wayne

[57] ABSTRACT

A pivaloylacetic acid ester is prepared at a high yield by decarbonylating a pivaloylpyruvic acid ester in gas or liquid phase in the presence of an inorganic oxide catalyst which comprises aluminum in an amount of 10% by weight or more in terms of aluminum oxide, and preferably is substantially free from heavy metals, for example, Fe, Cu, Ni, Mn, Cr, Mo and Co, and exhibits a high catalytic activity and chemical stability.

8 Claims, No Drawings

METHOD OF PRODUCING PIVALOYLACETIC ACID ESTER

BACKGROUND OF THE INVENTION

1. Field of the Invention

The present invention relates to a method of producing a pivaloylacetic acid ester. More particularly, the present invention relates to a method of producing a pivaloylacetic acid ester at a high yield by a decarbonylation reaction of a pivaloylpyruvic acid ester.

The pivaloylacetic acid ester is a very useful compound as an intermediate for synthesizing photographic materials.

2. Description of the Related Art

As conventional methods of producing a pivaloylacetic acid ester by a decarbonylation reaction of a pivaloylpyruvic acid ester, a method in which the pivaloylpyruvic acid ester is decarbonylated in the presence of a catalyst consisting of a metal selected from the group consisting of iron, copper, nickel, manganese, chromium, molybdenum and cobalt, as disclosed in Japanese Examined Patent Publication (Kokoku) No. 62-47170, and another method in which the pivaloylpyruvic acid ester is decarbonylated in the presence of ground or powderized glass, as disclosed in U.S. Pat. No. 2,527,306, are known.

Those conventional methods are not industrially satisfactory. In the latter method, since the above-mentioned catalysts exhibit unsatisfactory catalytic activity, the reaction must be carried out in the liquid phase in the presence of a large amount of the catalysts, 10 to 11% by weight based on the starting material, to produce the pivaloylacetic acid ester at a high yield, and thus the recovery and after-treatment procedures for the catalyst, after the completion of the reaction, are complicated. Especially, in the former method, since heavy metals are used as a catalyst, not only the recovery and after-treatment procedures of the catalyst are very complicated, but also there is a risk of producing a harmful metal carbonyl compound by a reaction of carbon monoxide, which is produced as a by-product of the catalystic reaction, with the heavy metals, and further, there is the significant problem that if iron powder, which has a highest catalytic activity, is used, the recovery of iron is low.

SUMMARY OF THE INVENTION

An object of the present invention is to provide a method of producing a pivaloylacetic acid ester at a high yield by decarbonylating a pivaloylpyruvic acid ester in the presence of a catalyst having a high catalytic activity and stability.

Another object of the present invention is to provide a method of producing a pivaloylacetic acid ester in the presence of a catalyst which can be easily recovered and subjected to after treatment.

The above-mentioned objects can be attained by the method of the present invention for producing a pivaloylacetic acid ester, comprising subjecting a pivaloylpyruvic acid ester to a decarbonylation reaction in the presence of an inorganic oxide catalyst containing aluminum in an amount of 10% by weight or more in terms of aluminum oxide.

Preferably, the inorganic oxide catalyst usable for the method of the present invention is substantially free from heavy metals.

DESCRIPTION OF THE PREFERRED EMBODIMENTS

In the method of the present invention, a pivaloylacetic acid ester is produced by decarbonylating a pivaloylpyruvic acid ester in the presence of an inorganic oxide catalyst containing aluminum in an amount of 10% by weight or more in terms of aluminum oxide. The aluminum-containing inorganic oxide materials are commonly known as carrier materials for various types of catalysts.

The pivaloylpyruvic acid ester usable for the present invention is preferably selected from those of the formula (I):

wherein R represents an alkyl group having 1 to 4 carbon atoms. Particularly, the pivaloylpyruvic acid esters usable for the present invention include methyl pivaloylpyruvate, ethyl pivaloylpyruvate, and n-propyl pivaloylpyruvate.

The pivaloylacetic acid ester produced by decarbonylating the corresponding pivaloylpyruvic acid ester is preferably selected from those of the formula (II):

wherein R represents an alkyl group having 1 to 4 carbon atoms.

The pivaloylacetic acid esters preferably include methyl pivaloylacetate, ethyl pivaloylacetate, and n-propyl pivaloylacetate.

In the process of the present invention, the decarbonylation reaction of the pivaloylpyruvic acid ester is carried out in the presence of an inorganic oxide catalyst containing aluminum in an amount of 10% by weight or more, preferably 30% by weight or more, more preferably 90% by weight or more, in terms of aluminum oxide. This type of inorganic oxide materials are popularly known as carrier materials for catalysts. Preferably, the inorganic oxide catalyst comprises 90% by weight or more of aluminum oxide ($Al_2O_3$).

If the content of the aluminum in the inorganic oxide catalyst is less than 10% by weight in terms of aluminum oxide ($Al_2O_3$), and the decarbonylation reaction is carried out in the liquid phase, the necessary reaction time becomes long. Also, when the decarbonylation reaction is carried out in the gas phase, an aluminum content of less than 10% by weight in terms of aluminum oxide ($Al_2O_3$) causes the amount of the catalyst necessary to obtain a satisfactory conversion of the pivaloylpyruvic acid ester to increase, and the thermal decomposition of the pivaloylpyruvic acid ester to be promoted, so as to reduce the yield of the resultant pivaloylacetic acid ester.

The inorganic oxide catalyst usable for the method of the present invention is preferably substantially free from heavy metals, for example, iron, copper, nickel, manganese, chromium, molybdenum and cobalt.

The aluminum-containing inorganic oxide carrier preferably comprises at least one member selected from the group consisting of aluminas, for example, α-alumina, γ-alumina, η-alumina, β-alumina and δ-alumina; zeolites, for example, zeolite A and zeolite B; synthetic zeolites (molecular sieves), for example, molecular sieve 3A, molecular sieve 4A, molecular sieve 5A and molecular sieve 13X; and silica alumina, all of which are preferably substantially free from the heavy metals. The zeolites and synthetic zeolites which have an ion-exchange performance may be ion-exchanged, at ion-exchange sites thereof, with ions other than heavy metal ions, for example, alkali metal ions, alkaline earth metal ions, hydrogen ions and/or ammonium ions.

For catalytic activity, it is preferable that the inorganic oxide catalyst be in the form of a plurality of particles having a size as small as possible. However, for handling ease, the inorganic oxide catalyst particles should preferably have a large size. Accordingly, the size of the inorganic oxide catalyst particles is controlled preferably to 0.05 to 10 mm, more preferably 0.5 to 3 mm.

In the method of the present invention, the decarbonylation reaction of the pivaloylpyruvic acid ester can be carried out in the liquid phase or gas phase.

In an embodiment of the liquid phase reaction, the pivaloylpyruvic acid ester is mixed with the inorganic oxide catalyst in a reactor, and the reaction is carried out by heating the mixture to a temperature of 100° C. to 280° C., preferably 150° C. to 200° C. There is no limitation to the pressure of the liquid phase reaction. Namely, the liquid phase reaction can be carried out under a reduced pressure, or an ambient atmospheric pressure or higher. Preferably, the liquid phase decarbonylation reaction is carried out under the ambient atmospheric pressure. In this case, the inorganic oxide catalyst is employed in an amount of 0.1 to 10% by weight, preferably 0.5 to 5% by weight, based on the weight of the starting compound, namely the pivaloylpyruvic acid ester. Usually, the decarbonylation reaction is completed within a time of 0.5 to 15 hours, preferably 0.5 to 5 hours. After the reaction, the target compound, namely the pivaloylacetic acid ester is isolated by distilling the reaction product mixture, and the inorganic oxide catalyst is recovered by, for example, filtration.

In an embodiment of the gas phase reaction, a feed gas prepared by, for example, vaporizing the pivaloylpyruvic acid ester by a vaporizer located outside of the reactor or vaporizing means located in the reactor and diluting the resultant vapor with an inert gas, for example, nitrogen gas, is continuously fed into a reaction pipe or tube packed with the inorganic oxide catalyst particles, to catalytically decarbonylate the pivaloylpyruvic acid ester. In this method, there is no limitation to the reaction pressure, and the reaction temperature of the reaction tube is preferably controlled to 150° C. to 300° C., more preferably 180° C. to 250° C., the space velocity of the pivaloylpyruvic acid ester-containing feed gas is preferably regulated to 50 to 3000 $hr^{-1}$, more preferably 100 to 1500 $hr^{-1}$ and the content of the pivaloylpyruvic acid ester in the feed gas is preferably adjusted to 1 to 300 g, more preferably 2 to 100 g, per liter of the inert gas. The gas phase reaction can be effected under a reduced pressure or the ambient atmospheric pressure or higher. In this gas phase reaction method, the resultant gaseous reaction product mixture delivered from the reaction pipe or tube is cool-condensed, the resultant condensed reaction product mixture is distilled to isolate the target compound.

The catalyst used in the gas phase reaction method and thus having a reduced activity, can be easily recovered by withdrawing it from the reaction pipe or tube. In this method of the present invention, the catalyst in the reaction tube can be easily regenerated (re-activated) by cleaning the catalyst with an organic solvent, for example, lower alkyl ketones having 1 to 5 carbon atoms, for example, acetone and methyl isopropyl ketone (MIPK), and lower alkyl alcohols having 1 to 5 carbon atoms, for example, methyl alcohol, ethyl alcohol and propyl alcohol. The regenerated inorganic oxide catalyst is reused for the decarbonylation reaction. Accordingly, the gas phase reaction of the method of the present invention can be continued over a long time period without renewing the inorganic oxide catalyst placed in the reactor.

EXAMPLES

The method of the present invention will be further explained by the following examples.

In the examples, the conversion of the pivaloylpyruvic acid ester and the yield of the pivaloylacetic acid ester were calculated based on the number of moles of starting material. In all the following examples and comparative examples, the decarbonylation reaction was carried out under the ambient atmospheric pressure.

Example 1

A glass reactor with a capacity of 50 ml was charged with 20 g of methyl pivaloylpyruvate in the liquid state and having a degree of purity of 98.9% by weight and 0.8 g of γ-alumina available under the trademark of Neobead RP-4A, made by Mizusawa Kagaku K. K., and having a particle size of 1 mm and an aluminum oxide ($Al_2O_3$) content of 94.5% by weight. In the reactor, the liquid charge was stirred at a temperature of 170° to 175° C. for 4 hours. As the reaction time elapsed, carbon monoxide was gradually generated. After the reaction was completed, the reaction product mixture was subjected to a gas chromatographic analysis. As a result, it was confirmed that methyl pivaloylacetate was produced in an amount of 15.4 g, which corresponds to a conversion of 91.8% and a yield of 91.8%. The catalyst was recovered in an amount of 0.8 g (recovery yield: 100%) by filtering the reaction product mixture, washing with methyl alcohol and drying under reduced pressure.

Example 2

A glass reactor with a capacity of 50 ml was charged with 20 g of liquid methyl pivaloylpyruvate having a degree of purity of 98.0% by weight and 0.8 g of γ-alumina available under the trademark of KHA-24, made from Sumitomo Kagaku K. K., and having a particle size of 1 mm and an aluminum oxide content of 99.7% by weight. In the reactor, the liquid charge was stirred at a temperature of 170° to 175° C. for 2 hours. As the reaction time elapsed, carbon monoxide was gradually generated. After the reaction was completed, the reaction product mixture was subjected to a gas chromatographic analysis. As a result, it was confirmed that methyl pivaloylacetate was produced in an amount of 14.3 g which corresponds to a conversion of 97.2% and a yield of 86.0%.

Example 3

The same procedures as in Example 1 were carried out with the following exceptions.

The inorganic oxide catalyst consisted of 0.8 g of α-alumina made by Kanto Kagaku K. K., and having a 70 to 230 mesh size and an aluminum oxide content of 99% by weight.

The decarbonylation reaction mixture was stirred at a temperature of 180° to 185° C. for 5 hours.

As a result of the analysis, it was found that methyl pivaloylacetate was produced in an amount of 14.3 g (conversion: 95.6%, yield: 85.4%).

Example 4

The same procedures as in Example 1 were carried out with the following exceptions.

The inorganic oxide catalyst consisted of 0.8 g of synthetic zeolite (available under the trademark of MOLECULAR SIEVE 3A 1/8, from Wako Junyaku K. K.), and having an aluminum content of 30% by weight in terms of aluminum oxide.

The decarbonylation reaction mixture was stirred at a temperature of 150° to 160° C. for 2 hours.

As a result of the analysis, it was found that methyl pivaloylacetate was produced in an amount of 14.7 g (conversion: 97.6%, yield: 87.7%).

Comparative Example 1

The same procedures as in Example 1 were carried out with the following exceptions.

No inorganic oxide catalyst was employed.

The liquid charge in the reactor was stirred at a temperature of 175° to 180° C. for 7 hours.

As a result of the analysis, it was found that methyl pivaloylacetate was produced in an amount of 6.8 g (conversion: 54.3%, yield: 40.2%).

Comparative Example 2

The same procedures as in Example 1 were carried out with the following exceptions.

The inorganic oxide catalyst consisted of 0.8 g of silica gel made by Ishizu Seiyaku K. K., and having a 60 to 100 mesh size.

The decarbonylation reaction mixture was stirred at a temperature of 190° to 200° C. for 7 hours.

As a result of the analysis, it was found that methyl pivaloylacetate was produced in an amount of 10.3 g (conversion: 77.4%, yield: 61.3%).

Comparative Example 3

The same procedures as in Example 1 were carried out with the following exceptions.

The inorganic oxide catalyst consisted of 0.8 g of zeolite pellets available under the trademark of HSD-640 NAD, made by Toso K. K., and having a diameter of 1 mm, a length of 10 mm and an aluminum content of 7.7% by weight in terms of aluminum oxide.

The decarbonylation reaction mixture was stirred at a temperature of 160° to 170° C. for 7 hours.

As a result of the analysis, it was found that methyl pivaloylacetate was produced in an amount of 11.5 g (conversion: 97.5%, yield: 68.1%).

Comparative Example 4

A glass reactor with a capacity of 50 ml was charged with 30 g of methyl pivaloylpyruvate in the liquid state and having a degree of purity of 96.7% by weight and 1.2 g of a catalyst consisting of electrolytic iron powder, made from Wako Junyaku K. K., and having a 100 mesh size. In the reactor, the liquid charge was stirred at a temperature of 200° C. for 3 hours. With the lapse of reaction time, carbon monoxide was gradually generated. After the reaction was completed, the reaction product mixture was subjected to a gas chromatographic analysis. As a result, it was confirmed that methyl pivaloylacetate was produced in an amount of 21.0 g which corresponds to a conversion of 100% and a yield of 85.4%. The catalyst was recovered in the same manner as in Example 1. Only 0.85 g of the catalyst was recovered at a recovery yield of 71%.

The reaction conditions and reaction results of Examples 1 to 4 and Comparative Examples 1 to 4 are shown in Table 1.

TABLE 1

| Example No. | | Type of catalyst | Reaction temperature (°C.) | Reaction time (hr) | Conversion of methyl pivaloyl-pyruvate (%) | Yield of methyl pivaloyl-acetate (%) |
|---|---|---|---|---|---|---|
| Example | 1 | γ-Alumina (Neobead RP-4A) | 170–175 | 4 | 91.8 | 91.8 |
|  | 2 | γ-Alumina (KHA-24) | 170–175 | 2 | 97.2 | 86.0 |
|  | 3 | α-Alumina | 180–185 | 5 | 95.6 | 85.4 |
|  | 4 | Synthetic zeolite | 150–160 | 2 | 97.6 | 87.7 |
| Comparative Example | 1 | None | 175–180 | 7 | 54.3 | 40.2 |
|  | 2 | Silica gel | 190–200 | 7 | 77.4 | 61.3 |
|  | 3 | Zeolite (HSD-640 NAD) | 160–170 | 7 | 97.5 | 68.1 |
|  | 4 | Electrolytic iron powder | 200 | 3 | 100 | 85.4 |

Example 5

A stainless steel reaction tube having an inside diameter of 29 mm and a length of 500 mm was packed with a catalyst consisting of 60 ml of γ-alumina available under the trademark of Neobead RP-4A from Mizusawa Kagaku K. K. and having a particle size of 1 mm and an aluminum oxide content of 94.5% by weight.

The reaction tube was heated at a temperature of 230° C. while flowing nitrogen gas at a flow rate of 350 ml/min through the reaction tube. Then, methyl pivaloylpyruvate having a degree of purity of 99.5% by weight was vaporized and added at a flow rate of 2 g/min to the nitrogen gas to start the decarbonylation reaction. One hour after the start of the reaction, a fraction of the gaseous reaction mixture passed through the catalyst layer during a 30 minute interval was cooled to condense it, and the resultant condensed reaction mixture was subjected to a gas chromatographic analysis. As a result, it was found that methyl pivaloylacetate was produced in an amount of 42.6 g (conversion: 99.0%, yield: 83.5%, space time yield: 1420 g/liter.hr). The space time yield (STY) in units of g/liter.hr of methyl pivaloylacetate was calculated in accordance with the following equation:

$$STY(g/liter.hr) = a/(b \times \theta)$$

wherein θ represents the reaction time in units of hr, a represents the amount in units of g of methyl pivaloylacetate produced in the reaction time θ, and b represents the amount in units of liter of the catalyst packed in the reaction tube.

Example 6

The same decarbonylation procedures as in Example 5 were carried out with the following exceptions.

The catalyst consisted of 30 ml of γ-alumina available under the trademark of Neobead RP-4A from Mizusawa Kagaku K. K. and having a particle size of 1 mm and an aluminum oxide content of 94.5% by weight.

The nitrogen gas was flowed at a rate of 100 ml/min.

One hour after the start of the reaction, a fraction of the reaction mixture passed through the catalyst layer during a 30 minute interval was cool-condensed, and the condensed reaction mixture was subjected to gas chromatographic analysis. As a result, it was found that methyl pivaloylacetate was produced in an amount of 41.3 g (conversion: 93.2%, yield: 81.4%, space time yield: 2753 g/liter.hr).

Example 7

The same decarbonylation procedures as in Example 5 were carried out with the following exceptions.

The catalyst consisted of 60 ml of γ-alumina available under the trademark of Neobead DB-48 from Mizusawa Kagaku K. K. and having a particle size of 3 mm and an aluminum oxide content of 95.3% by weight.

The nitrogen gas was flowed at a rate of 25 ml/min.

One hour after the start of the reaction, a fraction of the reaction mixture passed through the catalyst layer during a 30 minute interval was cool-condensed, and the condensed reaction mixture was subjected to gas chromatographic analysis. As a result, it was found that methyl pivaloylacetate was produced in an amount of 45.2 g (conversion: 95.5%, yield: 88.8%, space time yield: 1507 g/liter.hr).

Example 8

The same decarbonylation procedures as in Example 5 were carried out with the following exceptions.

The catalyst consisted of 30 ml of γ-alumina available under the trademark of Neobead GB-45 from Mizusawa Kagaku K. K. and having a particle size of 3 mm and an aluminum oxide content of 100% by weight.

The nitrogen gas was flowed at a flow rate of 100 ml/min.

The flow rate of the methyl pivaloylpyruvate was changed to 1 g/min.

One hour after the start of the reaction, a fraction of the reaction mixture passed through the catalyst layer during a 30 minute interval was cool-condensed, and the condensed reaction mixture was subjected to gas chromatographic analysis. As a result, it was found that methyl pivaloylacetate was produced in an amount of 22.0 g (conversion: 90.8%, yield: 86.2%, space time yield: 1467 g/liter.hr).

Example 9

The same decarbonylation procedures as in Example 5 were carried out with the following exceptions.

The catalyst consisted of 60 ml of γ-alumina available under the trademark of Neobead RP-4B from Mizusawa Kagaku K. K. and having a particle size of 1 mm and an aluminum oxide content of 94.5% by weight.

The nitrogen gas was flowed at a flow rate of 100 ml/min.

The flow rate of the methyl pivaloylpyruvate was changed to 4 g/min.

One hour after the start of the reaction, a fraction of the reaction mixture passed through the catalyst layer during a 15 minute interval was cool-condensed, and the condensed reaction mixture was subjected to gas chromatographic analysis. As a result, it was found that methyl pivaloylacetate was produced in an amount of 47.9 g (conversion: 96.5%, yield: 94.0%, space time yield: 3193 g/liter.hr).

Comparative Example 5

The same decarbonylation procedures as in Example 5 were carried out with the following exceptions.

No catalyst was employed.

One hour after the start of the reaction, a fraction of the reaction mixture passed through the catalyst layer during a 30 minute interval was cool-condensed, and the condensed reaction mixture was subjected to gas chromatographic analysis. As a result, it was found that methyl pivaloylacetate was produced in an amount of 0.036 g (conversion: 0.14%, yield: 0.14%).

Comparative Example 6

The same decarbonylation procedures as in Example 5 were carried out with the following exceptions.

The catalyst consisted of 30 ml of glass beads having a particle size of 2 mm and an aluminum content of 2.0% by weight in terms of aluminum oxide.

One hour after the start of the reaction, a fraction of the reaction mixture passed through the catalyst layer during a 30 minute interval was cool-condensed, and the condensed reaction mixture was subjected to gas chromatographic analysis. As a result, it was found that methyl pivaloylacetate was produced in an amount of 0.18 g (conversion: 0.36%, yield: 0.36%, space time yield: 12 g/liter.hr).

Comparative Example 7

The same decarbonylation procedures as in Example 5 were carried out with the following exceptions.

The catalyst consisted of 30 ml of silica gel available under the trademark of Silbead N from Mizusawa Kagaku K. K. and having a particle size of 1 mm and an alumium content of 2.0% by weight in terms of aluminum oxide.

The nitrogen gas was flowed at a flow rate of 100 ml/min.

One hour after the start of the reaction, a fraction of the reaction mixture passed through the catalyst layer during a 60 minute interval was cool-condensed, and the condensed reaction mixture was subjected to gas chromatographic analysis. As a result, it was found that methyl pivaloylacetate was produced in an amount of 11.0 g (conversion: 15.5%, yield: 10.8%, space time yield: 367 g/liter.hr).

Comparative Example 8

The same decarbonylation procedures as in Example 5 were carried out with the following exceptions.

The catalyst consisted of 30 ml of zeolite pellets available under the trademark of HSD-640 AND from Toso K. K. and having a diameter of 1 mm, a length of 10 mm and an aluminum content of 7.7% by weight in terms of aluminum oxide.

The nitrogen gas was flowed at a flow rate of 100 ml/min.

One hour after the start of the reaction, a fraction of the reaction mixture passed through the catalyst layer during a 60 minute interval was cool-condensed, and the condensed reaction mixture was subjected to gas chromatographic analysis. As a result, it was found that methyl pivaloylacetate was produced in an amount of 10.6 g (conversion: 17.2%, yield: 10.4%, space time yield: 353 g/liter.hr).

Comparative Example 9

The same decarbonylation procedures as in Example 5 were carried out with the following exceptions.

The catalyst consisted of 30 ml of stainless steel filler pellets available under the trademark of Helipack from Sogorikagaku Glass Kenkyusho and having dimensions of 1.25×2.5×2.5 mm.

The methyl pivaloylpyruvate vapor was added at a flow rate of 1 g/min to the nitrogen gas.

One hour after the start of the reaction, a fraction of the reaction mixture passed through the catalyst layer during a 30 minute interval was cool-condensed, and the condensed reaction mixture was subjected to gas chromatographic analysis. As a result, it was found that methyl pivaloylacetate was produced in an amount of 0.33 g (conversion: 1.9%, yield: 1.3%, space time yield: 22 g/liter.hr).

The reaction conditions and results of Examples 5 to 9 and Comparative Examples 5 to 9 are shown in Table 2.

reaction was 45.5 g (conversion: 93.1%, yield: 89.3% and space time yield: 1011 g/liter.hr).

Further, the amount of methyl pivaloylacetate produced during a 30 minute interval, 28 hours after the start of the reaction was 44.9 g (conversion: 91.4%, yield: 88.1% and space time yield: 998 g/liter.hr).

Example 11

The same reaction procedures as in Example 9 were carried out with the following exceptions.

The catalyst consisted of 50 ml of γ-alumina available under the trademark of Neobead RP-4B from Mizusawa Kagaku K. K. and having a particle size of 1 mm and an aluminum oxide content of 94.5% by weight.

The flow rate of the methyl pivaloylpyruvate was changed to 2 g/min.

During a 30 minute interval 2 hours after the start of the reaction, a fraction of the reaction mixture passed through the catalyst layer was sampled and subjected to the gas chromatographic analysis. It was found that methyl pivaloylacetate was produced in an amount of 48.1 g (conversion: 97.1%, yield: 94.4% space time yield: 1924 g/liter.hr).

TABLE 2

| | | | | | | Flow rate of methyl pivaloyl-pyruvate | Conversion of methyl pivaloyl-pyruvate | Yield of methyl pivaloyl-acetate | Space time yield of methyl pivaloyl-acetate |
|---|---|---|---|---|---|---|---|---|---|
| Example No. | | Catalyst Type | Amount | Flow rate of nitrogen gas (ml/min) | Reaction temperature (°C.) | (g/min) | (%) | (%) | (g/l · hr) |
| Example | 5 | γ-Alumina (Neobead RP-4A) | 60 ml | 350 | 230 | 2 | 99.0 | 83.5 | 1420 |
| | 6 | γ-Alumina (Neobead RP-4A) | 30 ml | 100 | 230 | 2 | 93.2 | 81.4 | 2753 |
| | 7 | γ-Alumina (Neobead DB-48) | 60 ml | 25 | 230 | 2 | 95.5 | 88.8 | 1507 |
| | 8 | γ-Alumina (Neobead GB-45) | 30 ml | 100 | 230 | 1 | 90.8 | 86.2 | 1467 |
| | 9 | γ-Alumina (Neobead RP-4B) | 60 ml | 100 | 230 | 4 | 96.5 | 94.0 | 3193 |
| Comparative Example | 5 | None | | 350 | 230 | 2 | 0.14 | 0.14 | — |
| | 6 | Glass beads | 30 ml | 350 | 230 | 2 | 0.36 | 0.36 | 12 |
| | 7 | Silica gel (Silbead N) | 30 ml | 100 | 230 | 2 | 15.5 | 10.8 | 367 |
| | 8 | Zeolite (HSD-640 NAD) | 30 ml | 100 | 230 | 2 | 17.2 | 10.4 | 353 |
| | 9 | Stainless steel filler | 30 ml | 350 | 230 | 1 | 1.9 | 1.3 | 22 |

Example 10

The same reaction procedures as in Example 9 were carried out with the following exceptions.

The catalyst consisted of 90 ml of γ-alumina available under the trademark of Neobead RP-4B from Mizusawa Kagaku K. K. and having a particle size of 1 mm and an aluminum oxide content of 94.5% by weight.

The flow rate of the methyl pivaloylpyruvate was changed to 2 g/min.

After 2 hours from the start of the reaction, a fraction of the reaction mixture passed through the catalyst layer was sampled for 30 minutes and subjected to the gas chromatographic analysis. It was found that methyl pivaloylacetate was produced in an amount of 44.1 g (conversion: 99.2%, yield: 86.8% space time yield: 980 g/liter.hr).

The amount of methyl pivaloylacetate produced during a 30 minute interval, 10 hours after the start of the reaction was 48.8 g (conversion: 98.7%, yield: 95.8%, and space time yield: 1084 g/liter.hr).

Also, the amount of methyl pivaloylacetate produced during a 30 minute interval, 20 hours after the start of the reaction was The amount of methyl pivaloylacetate produced during a 30 minute interval 10 hours after the start of the reaction was 48.1 g (conversion: 95.2%, yield: 94.4%, and space time yield: 1924 g/liter.hr).

Also, the amount of methyl pivaloylacetate produced during a 30 minute interval 20 hours after the start of the reaction was 38.6 g (conversion: 79.4%, yield: 75.8% and space time yield: 1545 g/liter.hr).

Since the activity of the catalyst appeared to be reduced, 24 hours after the start of the reaction, the feed of methyl pivaloylpyruvate was stopped and acetone was flowed at a rate of 3 g/min together with the nitrogen gas at a flow rate of 100 ml/min through the catalyst layer, at a temperature of 30° C. for 4 hours, and then the reaction charge in the reactor was heated at a temperature of 230° C. to restart the reaction.

During a 30 minute interval 4 hours after the restart of the reaction, methyl pivaloylacetate was produced in an amount of 49.4 g (conversion: 97.0%, yield: 96.9%, and space time yield: 1976 g/liter.hr).

Also, during a 30 minute interval 12 hours after the restart of the reaction, methyl pivaloylacetate was produced in an amount of 49.5 g (conversion: 97.3%, yield: 97.1% and space time yield: 1980 g/liter.hr).

Further, during a 30 minute interval 16 hours after the restart of the reaction, methyl pivaloylacetate was produced in an amount of 47.5 g (conversion: 93.5%, yield: 93.2% and space time yield: 1900 g/liter.hr).

Since the activity of the catalyst appeared to be slightly reduced, 18 hours after the restart of the reaction, the feed of methyl pivaloylpyruvate was stopped, acetone was flowed together with the nitrogen gas through the catalyst layer in the same manner as mentioned above for 2 hours, and then the reaction was re-started a second time in the same manner as mentioned above.

During a 30 minute interval 4 hours after the second restart of the reaction, methyl pivaloylacetate was produced in an amount of 49.2 g (conversion: 96.6%, yield: 96.4% and space time yield: 1968 g/liter.hr).

Also, during a 30 minute interval 6 hours after the second restart of the reaction, methyl pivaloylacetate was produced in an amount of 48.7 g (conversion: 95.8%, yield: 95.6% and space time yield: 1948 g/liter.hr).

As illustrated above, the method of the present invention effectively enables the pivaloylacetic acid ester to be easily produced at a high yield by the decarbonylation of the corresponding pivaloylpyruvic acid ester in the presence of a specific catalyst having a high activity and an enhanced stability.

The method of the present invention does not employ a metal catalyst which must be recovered or subjected to after-treatment by a complicated procedure and thus is free from the risk of generation of dangerous metal carbonyl compounds. Also, the method of the present invention can be continuously carried out in the gas phase over a long time period without renewing the catalyst, under safe conditions.

We claim:

1. A method of producing a pivaloylacetic acid ester, comprising subjecting a pivaloylpyruvic acid ester to a decarbonylation reaction in the presence of an inorganic oxide catalyst containing aluminum in an amount of 10% by weight or more in terms of aluminum oxide and wherein the decarbonylation reaction is carried out in the gas phase at a temperature of 150° to 300° C. by feeding a feed gas comprising an inert gas and the pivaloylpyruvic acid gas in an amount of 1 to 300 g per liter of the inert gas at a space velocity of 50 to 3000 hr$^{-1}$.

2. The method as claimed in claim 1, wherein the inorganic oxide catalyst is substantially free from heavy metals.

3. The method as claimed in claim 1, wherein the inorganic oxide catalyst comprises 90% by weight or more of at least one alumina.

4. The method as claimed in claim 1, wherein the inorganic oxide catalyst comprises at least one member selected from the group consisting of aluminas, zeolites, synthetic zeolites and silica-aluminas.

5. The method as claimed in claim 1, wherein the inorganic oxide catalyst is in the form of a plurality of particles having a size of 0.05 to 10 mm.

6. The method as claimed in claim 1, wherein the pivaloylpyruvic acid ester is selected from those of the formula (I):

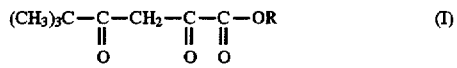

wherein R represents an alkyl group having 1 to 4 carbon atoms.

7. The method as claimed in claim 1, wherein the resultant reaction product mixture is subjected to a distillation to isolate the pivaloylacetic acid ester.

8. The method as claimed in claim 1, further comprising cleaning the used inorganic oxide catalyst with an organic solvent to regenerate the catalyst and reusing the regenerated catalyst for the decarbonylation reaction.

* * * * *